(12) United States Patent
Agrawal et al.

(10) Patent No.: US 6,509,459 B1
(45) Date of Patent: *Jan. 21, 2003

(54) BASE PROTECTING GROUPS AND RAPID PROCESS FOR OLIGONUCLEOTIDE SYNTHESIS

(75) Inventors: Sudhir Agrawal, Shrewsbury, MA (US); Radhakrishnan P. Iyer, Shrewsbury, MA (US); Ivan Habus, Shrewsbury, MA (US); Dong Yu, Shrewsbury, MA (US)

(73) Assignee: Hybridon, Inc., Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/846,303

(22) Filed: Apr. 30, 1997

Related U.S. Application Data

(63) Continuation-in-part of application No. 08/606,915, filed on Feb. 26, 1996, now Pat. No. 5,962,674, and a continuation-in-part of application No. 08/598,320, filed on Feb. 8, 1996, now abandoned, and a continuation-in-part of application No. 08/570,390, filed on Dec. 11, 1995, now Pat. No. 5,955,599, and a continuation-in-part of application No. 08/519,318, filed on Aug. 25, 1995, now Pat. No. 6,140,482, and a continuation-in-part of application No. 08/518,921, filed on Aug. 24, 1995, now Pat. No. 5,614,622, and a continuation-in-part of application No. PCT/US96/08136, filed on Aug. 24, 1995, which is a continuation-in-part of application No. 08/457,198, filed on Jun. 1, 1995, now abandoned.

(51) Int. Cl.$^7$ ............................................. C07H 21/00
(52) U.S. Cl. .................. 536/25.3; 536/25.31; 536/23.1; 435/6; 435/91.1; 435/375; 435/372; 435/442
(58) Field of Search ................................ 536/25.3, 23.1, 536/25.33; 435/6, 91.1, 375, 372, 442

(56) References Cited

U.S. PATENT DOCUMENTS

| | | | |
|---|---|---|---|
| 5,149,798 A | | 9/1992 | Agrawal et al. |
| 5,955,599 A | * | 9/1999 | Iyer et al. .................. 536/25.3 |
| 5,962,674 A | * | 10/1999 | Iyer et al. ................. 536/25.34 |

FOREIGN PATENT DOCUMENTS

WO    WO 96/39414    12/1996

OTHER PUBLICATIONS

*Methods in Molecular Biology, vol. 20: Protocols for Oligonucleotides and Analogs,* pp. 165–189 (S. Agrawal, Ed., Humana Press, 1993).
*Oligonucleotides and Analogues: A Practical Approach,* pp. 87–108 (F. Eckstein, Ed., 1991).
Agrawal et al. (1995) *Current Op. In Biotech.* 6:12–19.
Khorona et al. (1972) *J. Molec. Biol.* 72:209–217.
Beaucage (1981) *Tetrahedron Lett.* 22:1859–1862.
Agrawal et al. (1987) *Tetrahedron Lett.* 28:3539–3542.
Connolly et al. (1984) *Biochemistry* 23:3443–3453.
Jager et al. (1988) *Biochemistry* 27:7237–7246.
Agrawal et al. (1988) *Proc. Natl. Acad. Sci. USA* 85:7079–7083.
Padmapriya et al. (1994) *Antisense Res. Dev.* 4:185–199.
Ravikumar et al. (1994) *Tetrahedron Lett.* 50:9255–9266.
Theisen et al. (1994) *Nucleoside & Nucleotides* 12:1033–1046.
Iyer et al. (1995) *Nucleosides & Nucleotides* 14:1349–1357.
Reddy et al. (1994) *Tetrahedron Lett.* 35:4311–4314.
Galbraith et al. (1994) *Antisense Research & Development* 4:201–206.
Henry et al. (1994) *Pharm. Res.* 11:PPDM8982.
Miller et al. (1986) *Biochemistry* 25:5092–5095.
Agrawal et al. (1987) *Tetrahedron Lett.* 28:3539–3542.
Miller et al. (1971) *J. Am. Chem. Soc.* 93:6657–6665.
Sonveaux in *Methods in Molecular Biology, Vol. 26: Protocols for Oligonucleotide Conjugates* pp. 1–36 (S. Agrawal Ed., Humana Press, 1994).
Moody et al. (1989) *Nucl. Acids Res.* 17:4769–4783.
Buck et al. (1990) *Science* 248:208–212.
Buck et al. (1990) *Science* 249:125–126.
Alul et al. (1991) *Nucl. Acids. Res.* 19:1527–1532.
Kujipers et al. (1990) *Nucl. Acids. Res.* 18:5197–5205.
Vinogradov et al. (1993) *Tetrahedron Letters* 34:5899–5902.
Hayakawa et al. (1995) *J. Org. Chem.* 60:925–930.
Iyer et al. (1995) *J. Org. Chem.* 60:5388–5389.
Beaucage et al. (1992) *Tetrahedron* 48:2223–2311.
Iyer et al. (1995) *Tetrahedron Asymemetry* 6:1051–1054.
Agrawal et al. (1992) *Antisense Research and Development* 2:261–266.
Debenham et al. (1995) *J. Am. Chem. Soc.* 117:3302–3303.
Iyer et al. (1995) *J. org. Chem.* 60:8132–8133.
Madsen et al. (1995) *J. Org. Chem.* 60:7920–7925.

* cited by examiner

*Primary Examiner*—James O. Wilson
(74) *Attorney, Agent, or Firm*—Hale and Dorr LLP

(57) ABSTRACT

The invention provides new processes for synthesizing oligonucleotides that allow for deprotection of the oligonucleotide under more rapid and/or more mild conditions than existing methods.

The invention further provides a nucleoside base protecting group that is stable under oligonucleotide synthesis conditions, but which can be removed under more mild conditions than existing protecting groups, as well as nucleoside synthons having such base protecting groups. The invention also provides oligonucleotides containing any of a variety of base labile functionalities and methods for using such oligonucleotides.

5 Claims, No Drawings

BASE PROTECTING GROUPS AND RAPID PROCESS FOR OLIGONUCLEOTIDE SYNTHESIS

This is a continuation-in-part of U.S. Ser. No. 08/606,915, filed Feb. 26, 1996, now U.S. Pat. No. 5,962,674; Ser. No. 08/598,320, filed Feb. 8, 1996 now abandoned; Ser. No. 08/570,390, filed Dec. 11, 1995, now U.S. Pat. No. 5,955,599; Ser. No. 08/519,318, filed Aug. 25, 1995, now U.S. Pat. No. 6,140,482; and Ser. No. 08/518,921, filed Aug. 24, 1995, now U.S. Pat. No. 5,614,622; and international application PCT/US96/08136 filed on Aug. 24, 1995; all of which are continuations-in-part of U.S. Ser. No. 08/457,198, filed Jun. 1, 1995, now abandoned.

BACKGROUND OF THE INVENTION

1. Field of the Invention

The invention relates to the chemical synthesis of oligonucleotides and to chemical entities and processes useful in such synthesis.

2. Summary of the Related Art

Oligonucleotides have become indispensible tools in modern molecular biology, being used in a wide variety of techniques, ranging from diagnostic probing methods to PCR to antisense inhibition of gene expression. This widespread use of oligonucleotides has led to an increasing demand for rapid, inexpensive and efficient methods for synthesizing oligonucleotides.

The synthesis of oligonucleotides for antisense and diagnostic applications can now be routinely accomplished. See e.g., *Methods in Molecular Biology, Vol 20: Protocols for Oligonucleotides and Analogs* pp. 165–189 (S. Agrawal, Ed., Humana Press, 1993); *Oligonucleotides and Analogues: A Practical Approach,* pp. 87–108 (F. Eckstein, Ed., 1991); and Uhlmann and Peyman, supra. Agrawal and Iyer, *Curr. Op. in Biotech.* 6: 12 (1995); and *Antisense Research and Applications* (Crooke and Lebleu, Eds., CRC Press, Boca Raton, 1993). Early synthetic approaches included phosphodiester and phosphotriester chemistries. Khorana et al., *J. Molec. Biol.* 72: 209 (1972) discloses phosphodiester chemistry for oligonucleotide synthesis. Reese, *Tetrahedron Lett.* 34: 3143–3179 (1978), discloses phosphotriester chemistry for synthesis of oligonucleotides and polynucleotides. These early approaches have largely given way to the more efficient phosphoramidite and H-phosphonate approaches to synthesis. Beaucage and Caruthers, *Tetrahedron Lett.* 22: 1859–1862 (1981), discloses the use of deoxynucleoside phosphoramidites in polynucleotide synthesis. Agrawal and Zamecnik, U.S. Pat. No. 5,149,798 (1992), discloses optimized synthesis of oligonucleotides by the H-phosphonate approach.

Both of these modem approaches have been used to synthesize oligonucleotides having a variety of modified internucleotide linkages. Agrawal and Goodchild, *Tetrahedron Lett.* 28: 3539–3542 (1987), teaches synthesis of oligonucleotide methylphosphonates using phosphoramidite chemistry. Connolly et al., *Biochemistry* 23: 3443 (1984), discloses synthesis of oligonucleotide phosphorothioates using phosphoramidite chemistry. Jager el al., *Biochemistry* 27: 7237 (1988), discloses synthesis of oligonucleotide phosphoramidates using phosphoramidite chemistry. Agrawal et al., *Proc. Antl. Acad. Sci. USA* 85: 7079–7083 (1988), discloses synthesis of oligonucleotide phosphoramidates and phosphorothioates using H-phosphonate chemistry.

Solid phase synthesis of oligonucleotides by each of the foregoing processes involves the same generalized protocol. Briefly, this approach comprises anchoring the 3'-most nucleoside to a solid support functionalized with amino and/or hydroxyl moieties and subsequently adding the additional nucleosides in stepwise fashion. Desired internucleoside linkages are formed between the 3' functional group of the incoming nucleoside and the 5' hydroxyl group of the 5'-most nucleoside of the nascent, support-bound oligonucleotide.

Refinement of methodologies is still required, however, particularly when making a transition to large-scale synthesis (10 μmol to 1 mmol and higher). See Padmapriya et al., *Antisense Res. Dev.* 4: 185 (1994). Several modifications of the standard phosphoramidite processes have already been reported to facilitate the synthesis (Padmapriya et al., supra; Ravikumar et al., *Tetrahedron* 50: 9255 (1994); Theisen et al., *Nucleosides & Nucleotides* 12: 43 (1994); and Iyer et al., *Nucleosides & Nucleotides* 14: 1349 (1995)) and isolation (Kuijpers et al. *Nucl. Acids Res.* 18: 5197 (1990); and Reddy et al., *Tetrahedron Lett.* 35: 4311 (1994)) of oligonucleotides.

The routine synthesis of oligonucleotides is presently carried out using various N-acyl protecting groups for the nucleoside bases, such as isobutyryl (for guanine), and benzoyl for adenine and cytosine. After the synthesis of the oligonucleotides is carried out using either phosphoramidite chemistry or H-phosphonate chemistry, the protecting groups are removed by treatment with ammonia at 55–60° C. for 5–10 hours. Using these protecting groups, PO oligonucleotides and other modified oligonucleotides can be synthesized. However, it would be greatly advantageous to be able to carry out such synthesis more rapidly, which would be possible if the time required for removal of the protecting groups could be reduced.

In addition, when currently available deprotection conditions are used, in certain instances where modified oligonucleotides are functionalized with base-sensitive groups, the functionalities often get removed while the deprotection is being carried out. Examples of such base-sensitive modified oligonucleotides include, ribonucleoside-containing oligonucleotides, methylphosphotriester oligonucleotides, phosphoramidates, etc.

One such example is the large-scale synthesis of RNA which is required for the ribozyme-based therapeutic strategies. Such synthesis presents special challenges due to two factors. These are, first, 3'-5' to 2'-5' internucleotide chain migration during preparation of nucleoside monomer precursors, during synthesis, and during removal of protecting groups from the RNA, and second, degradation of RNA. Use of classical protecting groups compounds these factors. For successful RNA synthesis, it is essential that the 2' hydroxyl protecting group remains intact until the final deprotection step and that following its removal, the 2' hydroxyl group does not attack the vicinal phosphodiester groups and thereby promote cleavage or migration of the internucleotidic linkages.

Another example is that current synthesis procedures allow the synthesis of some, but not all possible oligonucleotide phosphoramidates, because some of these compounds are labile under the highly alkaline conditions required for deprotection of the nucleoside base. Oligonucleotides containing primary phosphoramidate internucleoside linkages, for example, have not previously been possible to synthesize for this reason. In the case of the oligonucleotide phosphoramidates, this inability to synthesize oligonucleotides containing primary phosphoramidate internucleoside linkages has probably slowed their development as optimally useful compounds for molecular biology applications and the antisense therapeutic approach. This is likely because the oligonucleotide phosphoramidates that have been developed all have relatively large chemical substituents in place of one of the nonbridging oxygen atoms on the phosphate backbone, which may lead to steric hindrance in the ability of the oligonucleotide to bind to its target. It would be valuable to have internucleotidic primary phosphoramidate linkages, since incorporation of such non-ionic linkages could result in a reduction in oligonucleotide side effects that are attributable to the polyanionic character of the oligonucleotides. For example, Galbraith et al., Antisense Research and Development 4: 201–206 (1994) disclose complement activation by oligonucleotides. Henry et al., Pharm. Res. 11: PPDM8082 (1994) discloses that oligonucleotides may potentially interfere with blood clotting.

Yet another example is the synthesis of oligonucleotides containing methylphosphonate internucleoside linkages. Various methodologies have been used to synthesize such oligonucleotides. Miller et al., Biochemistry 25: 5092–5095 (1986), discloses an early methodology using a polymer support. Agrawal and Goodchild, Tetrahedron Lett. 28: 3539–3542 (1987), teaches a more generally applicable phosphoramidite approach using a controlled pore glass (CPG) support. All of the existing approaches, however, are inherently limited by the susceptibility of the methylphosphonate linkage to hydrolysis by base, which precludes the use of the usual deprotection step, which employs prolonged treatment with 28% ammonium hydroxide. Some attempts to deal with this problem have included the use of N-isobutyryl-protected cytidine nucleoside phosphonamidite monomers in conjunction with $dA^{bz}$ and $dG^{iBu}$ monomers, followed by deprotection using initial exposure of the oligomer to 10% ammonium hydroxide in acetonitrile/ethanol at room temperature, then prolonged exposure to ethylenediamine. Also used has been pretreatment of the protected oligonucleotide with hydrazine hydrate in pyridine/acetic acid, followed by prolonged exposure to ethylene diamine/ethanol. Although these approaches have provided somewhat inconvenient answers to certain problems, they have created problems of their own for large scale synthesis of chimeric oligonucleotides, which have segments of different internucleosidic linkages. For example, the $dG^{iBu}$-methylphosphonamidite monomer is insoluble in acetonitrile, which is the solvent commonly used with most other phosphoramidite monomers. Consequently, prior to each coupling step at which this monomer is added, it is necessary to thoroughly wash the monomer delivery lines and the synthesis column with a solvent in which the $dG^{iBu}$ monomer is soluble, such as anhydrous peroxide-free THF or $CH_3CN/CH_2Cl_2$, to avoid precipitation of this monomer in the delivery lines or column.

Still another example is synthesis of oligonucleotides containing methyphosphotriester internucleoside linkages. Such oligonucleotides could have many beneficial properties, because the methyl phosphotriester group is nonionic, but is similar in size and molecular shape to the phosphodiester linkage. Such nonionic methyl phosphotriester linkages could result in a reduction in oligonucleotide side effects that are attributable to the polyanionic character of the oligonucleotides.

The art has recognized the desirability of incorporating methyl phosphotriester internucleotide linkages into oligonucleotides and many attempts have been made to make and use such oligonucleotides. However, these attempts have subsequently been discovered to be unsuccessful. Miller et al., J. Am. Chem. Soc. 93: 6657–6665 (1971), discloses alleged methylphosphotriester DNA synthesis by methylation of the phosphate using p-toluenesulphonyl chloride and methanol. Moody et al., Nucl. Acids Res. 17: 4769–4783 (1989), discloses regiospecific inhibition of DNA duplication by oligonucleotides synthesized according to the process of Miller et al. Buck et al., Science 248: 208–212 (1990), discloses that oligonucleotides according to Moody et al. inhibit viral infectivity of HIV-1. However, Buck et al., Science 249: 125–126 (1990), retracts the earlier Buck et al. report and discloses that oligonucleotides synthesized according to this process do not contain methyl phosphotriester internucleotide linkages.

The difficulty in synthesizing oligonucleotides having methyl phosphotriester internucleotide linkages is due to the lability of the methyl ester bond under the oligonucleotide synthesis conditions used in the steps of deprotecting the nucleoside bases and cleaving the oligonucleotides from the solid support. Alul et al., Nucl. Acids Res. 19: 1527–1532 (1991), addressed the problem of cleaving the oligonucleotide from the solid support by introducing an oxalyl-type linker that can be cleaved under conditions that preserve the methyl ester bond. However, the problem of base deprotection was not addressed, so they were only able to synthesize methyl phosphotriester-linked thymidines, which lack an exocyclic amino group and thus do not require deprotection. Kuijpers et al., Nucl. Acids Res. 18: 5197–5205 (1990), attempted to address the deprotection problem by treating the FMOC-protected nucleoside bases for 43 hours in potassium carbonate/methanol. Unfortunately, NMR analysis of their oligonucleotides revealed that considerable demethylation had occurred, resulting oligonucleotides having a mixture of methylphosphotriester and phosphodiester linkages. Similarly, Vinogradov et al., Tetrahedron Lett. 34: 5899–5902 (1993), attempted to solve the problem by using an isopropoxyacetyl group to protect the nucleoside bases, but found that at least 35–40% demethylation still occurred. Most recently, Hayakawa et al., J. Org. Chem. 60: 925–930 (1995), claimed to have synthesized a decamer oligonucleotide containing a single methyl phosphotriester internucleotide linkage. However, NMR data supporting this claim was absent. Moreover, the process utilized costly and toxic palladium, which could contaminate the oligonucleotide product and render it unsuitable for therapeutic applications. In addition, the process was not shown to be able to introduce multiple methylphosphotriester linkages into the oligonucleotide.

In other applications of oligonucleotides, it is desirable to have oligonucleotides still bound to the solid support. Such completely deprotected oligonucleotides still bound to the solid support can be useful in a variety of applications such as those involving isolation of transcription factors and other factors or elements that interact with oligonucleotides. They are also useful for solid-phase PCR, investigation into nucleic acid protein interactions by, for example, NMR, creation and use of combinatorial libraries, screening of nucleic acid libraries, and solid support based hybridization probes (analogous to Southern and Northern blotting protocols). Creating such a support bound, deprotected oligonucleotide would be greatly aided by having a protecting group that could be removed by mild conditions that would not cleave the oligonucleotide from the support.

It would further be desirable to covalently attach certain ligands to oligonucleotides via ester or amide linkages. This would be most advantageously performed when the oligonucleotide is still bound to the solid support because most nucleophilic sites on the oligonucleotide will be blocked by protecting groups and thus will not interfere during ligand conjugation; also because the procedure is simplified by the ability to wash away reagents and solvents in the liquid phase.

These numerous examples clearly demonstrate a need for processes for oligonucleotide synthesis that allow for deprotection of the oligonucleotide under more mild conditions than existing processes. There is further a need for nucleoside synthons having new base protecting groups that are stable under oligonucleotide synthesis conditions, but which can be removed under more rapid and/or more mild conditions than existing protecting groups. Finally, there is a need for oligonucleotides which contain any of a variety of base labile functionalities. An ideal solution to these needs would require a process which allows oligonucleotides to be recovered at higher yields, while simultaneously providing milder conditions.

BRIEF SUMMARY OF THE INVENTION

The invention provides new processes for synthesizing oligonucleotides that allow for deprotection of the oligonucleotide under more rapidly and under more mild conditions than existing processes. The invention further provides a nucleoside base protecting group that is stable under oligonucleotide synthesis conditions, but which can be removed under more mild conditions than existing protecting groups, as well as nucleoside synthons having such base protecting groups. The invention also provides oligonucleotides containing any of a variety of base labile functionalities and methods for using such oligonucleotides.

In a first aspect, the invention provides a novel nucleoside base protecting group having the general structure I:

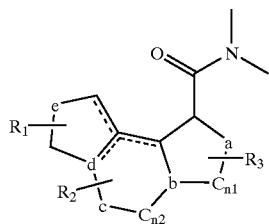

wherein n1, n2 and n3 are independently 0–10, wherein a, b, c, d and e are each independently hydrogen, carbon or nitrogen, and wherein the ring structure bearing substituent $R_3$ shown may be aromatic or heterocyclic, wherein the nitrogen displayed is the protected amino moiety of the nucleoside base, wherein $R_1$, $R_2$ and $R_3$ are independently hydrogen, or an alkyl, aryl, aralkyl, ether, hydroxy, nitrile, nitro, ester, carboxyl, or aldehyde group, and wherein dotted lines represent alternative exocyclic or endocyclic double bonds. In a preferred embodiment, a is hydrogen when n1 is 0 and is carbon or nitrogen when $n_1$ is 1–10, b is hydrogen when n1 and n2 are both 0 and is carbon or nitrogen when either or both n1 and n2 are 1–10, c is hydrogen when n2 is 0 and is carbon or nitrogen when n2 is 1–10, and e is hydrogen when n3 is 0 and is carbon or nitrogen when n3 is 1–10. In a particularly preferred embodiment, compound I has n1, n2 and n3 values of 0, and a, b, c, d and e are each hydrogen, and the protecting group takes the form N-pent-4-enoyl, i.e., $CH_2=CH(CH_2)_2CO-$ (II). Compounds I and II protect the nucleoside base amino moieties by forming amide linkages, as in:

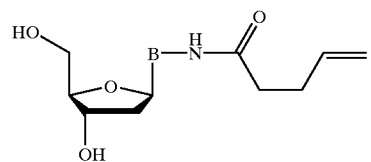

where the nitrogen displayed is the protected amino moiety of the base B.

Base protecting group I and the preferred embodiment II are particularly advantageously used because such protecting group can be removed chemoselectively by treatment with a chemoselective removing agent. Thus, in a second aspect, the invention provides a process for synthesizing oligonucleotides that allows for removal of base protecting groups under more mild conditions than existing processes. This new process comprises sequentially coupling nucleoside synthons having base protecting groups according to the invention to produce a base-protected oligonucleotide, followed by deprotection using a chemoselective removing agent. The process according to the invention can utilize any known or otherwise suitable oligonucleotide synthesis chemistry, including the well known H-phosphonate, phosphoramidite and phosphotriester chemistries.

The use of this new process provides numerous advantages. For example the process's mild procedure for removing the protecting group without affecting the integrity of other functionalities present in the oligonucleotide makes it possible to prepare novel analogs of oligonucleotides such as ribonucleoside-containing oligonucleotides, alkylphosphotriesters, certain base-sensitive phosphoramidate and other base-sensitive oligonucleotides.

Besides being able to synthesize oligonucleotides bearing "sensitive" functionalities, the process according to this aspect of the invention can also be used in the routine synthesis of various oligonucleotides as in case of the conventional protecting groups. In addition, this new process allows for synthesis of oligonucleotides still bound to any type of solid support.

Importantly, the processes according to this aspect of the invention are compatible with and can be used in conjunction with any of the well known oligonucleotide synthetic chemistries, including the H-phosphonate, phosphoramidate and phosphotriester chemistries. Consequently, the processes according to this aspect of the invention can be used to synthesize oligonucleotides having ribonucleosides and/or primary phosphoramidate, alkylphosphonate, or methylphosphonate linkages at some internucleoside positions and other linkages at other internucleoside positions.

In a third aspect, the invention provides novel synthons for use in synthesis of oligonucleotides having base-sensitive functionalities.

One such novel synthon can be used to prepare portions of the oligonucleotide containing deoxyribonucleosides linked by any known internucleoside linkage. This monomer synthon according to the invention has the general structure III:

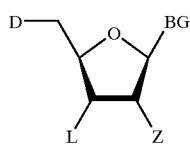

III wherein B is a nucleoside base, D is a 5'-OH blocking group (see e.g. Sonveaux in *Methods in Molecular Biology, Vol 26: Protocols for Oligonucleotide Conjugates* pp. 28–36 (S. Agrawal, Ed., Humana Press, 1994), preferably dimethoxytrityl or trityl, the protecting group (G) is the previously described structure I, or its preferred embodiment II, Z is hydrogen, —OG, —NG2, halogen (preferably Cl, Br or F), an —O-lower alkyl group containing 1–6 saturated or unsaturated carbon atoms, an —O-aryl or allyl group having 2–6 carbon atoms, wherein such alkyl, aryl or allyl group may be unsubstituted or may be substituted, e.g, with halogen, trifluoromethyl, cyano, nitroG, acylG, acyloxyg, alkoxyG, carboxyG, carbalkoxyG; and L is a phosphoramidite, H-phosphonate, or phosphotriester leaving group, including cyclic phosphoramidite leaving groups (see Iyer et al., J. Org. Chem. 60:5388–5389 (1995)). This synthon can be used alone, with any of the known synthons, or in conjunction with any of the following synthons.

Another such novel synthon is useful in the synthesis of oligonucleotides containing ribonucleosides. This ribonucleoside synthon according to the invention has the general structure IV:

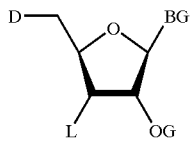

IV wherein B is a nucleoside base, D is a 5'-OH blocking group (see e.g Sonveaux in *Methods in Molecular Biology, Vol 26: Protocols for Oligonucleotide Conjugates* pp. 28–36 (S. Agrawal, Ed., Humana Press, 1994), preferably dimethoxytrityl or trityl, the protecting group (G) is the previously described structure I, or its preferred embodiment II, and L is a phosphoramidite, H-phosphonate, or phosphotriester leaving group, including cyclic phosphoramidite leaving groups (see Iyer et al., J. Org. Chem. 60:5388–5389 (1995)).

Another novel synthon according to this aspect of the invention is useful for synthesizing oligonucleotides containing primary phosphoramidate internucleoside linkages. This monomer synthon according to the invention has the general structure V:

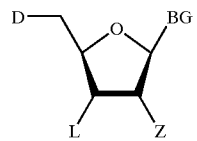

V wherein B is a nucleoside base, D is a 5'-OH blocking group (see e.g Sonveaux in *Methods in Molecular Biology, Vol 26: Protocols for Oligonucleotide Conjugates* pp. 28–36 (S. Agrawal, Ed., Humana Press, 1994), preferably dimethoxytrityl or trityl, the protecting group (G) is the previously described structure I, or its preferred embodiment II, Z is hydrogen, —OG, —NG2, halogen (preferably Cl, Br or F), an —O-lower alkyl group containing 1–6 saturated or unsaturated carbon atoms, an —O-aryl or allyl group having 2–6 carbon atoms, wherein such alkyl, aryl or allyl group may be unsubstituted or may be substituted, e.g., with halogen, trifluoromethyl, cyano, nitroG, acylG, acyloxyG, alkoxyG, carboxyG, carbalkoxyG; and L is an H-phosphonate or H-phosphonothioate leaving group.

Another novel synthon according to this aspect of the invention is useful for synthesizing oligonucleotides containing alkylphosphonate internucleoside linkages. This monomer synthon according to the invention has the general structure VI:

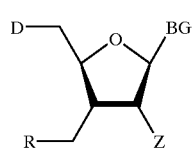

VI wherein B is a nucleoside base, D is a 5'-OH blocking group (see e.g. Sonveaux in *Methods in Molecular Biology, Vol 26: Protocols for Oligonucleotide Conjugates* pp. 28–36 (S. Agrawal, Ed., Humana Press, 1994), preferably dimethoxytrityl or trityl, R is an alkylphosphonamidite (preferably a methylphosphonamidite) group, Z is hydrogen, —OG, —NG2, halogen (preferably Cl, Br or F), an —O-lower alkyl group containing 1–6 saturated or unsaturated carbon atoms, an —O-aryl or allyl group having 2–6 carbon atoms, wherein such alkyl, aryl or allyl group may be unsubstituted or may be substituted, e.g., with halogen, trifluoromethyl, cyano, nitroG, acylG, acyloxyG, alkoxyG, carboxyG, carbalkoxyG; and the protecting group (G) is the previously described structure I, or its preferred embodiment II.

In a fourth aspect, the invention provides novel oligonucleotides containing from one to about all of a variety of base-sensitive functionalities. In a preferred embodiment, such oligonucleotides may contain from one to about all ribonucleotides and/or may contain from one to about all internucleoside linkages selected from the group consisting of primary phosphoramidate and methylphosphotriester linkages. In embodiments of oligonucleotides according to this aspect of the invention that have fewer than all primary phosphoramidate or methylphosphotriester internucleoside linkages, the other internucleoside linkages may be any of the known internucleoside linkages, or may be any internucleoside linkage not yet known that can be incorporated into an oligonucleotide according to a synthetic chemistry with which the process according to the invention is compatible. Oligonucleotides containing such a mixture of internucleoside linkages are referred to herein as mixed backbone oligonucleotides. In some preferred embodiments of mixed backbone oligonucleotides according to the invention, the internucleoside linkages that are not primary phosphoramidate linkages are selected from the group consisting of phosphodiester and phosphorothioate internucleoside linkages. In some preferred embodiments of mixed backbone oligonucleotides according to the invention, several adjacent nucleosides comprising one region of the oligonucleotide are connected by primary phosphoramidate linkages, and several other adjacent nucleosides comprising another region of the oligonucleotide are connected by a different type of internucleoside linkage. These preferred oligonucleotides are referred to herein as "chimeric" oligonucleotides.

Oligonucleotides according to the invention are useful for a variety of purposes. For example, they can be labeled with a reporter group and used as probes in conventional nucleic acid hybridization assays. They can also be used as antisense "probes" of specific gene function by being used to block the expression of a specific gene in an experimental cell culture or animal system and to evaluate the effect of blocking such specific gene expression. In this use, oligonucleotides according to the invention are preferable to traditional "gene knockout" approaches because they are easier to use and can be used to block specific gene expression at selected stages of development or differentiation. Finally, oligonucleotides according to the invention are useful in the antisense therapeutic approach. In this use, oligonucleotides according to the invention should have reduced polyanion-mediated side effects and improved cellular uptake.

In a fifth aspect, the invention provides methods for using oligonucleotides containing any of a variety of base-sensitive functionalities to control the expression of specific genes. Such methods comprise administering oligonucleotides according to the invention to cells or to animals, including humans. These methods may be used to assess gene function, or as a therapeutic approach to the treatment of diseases resulting from aberrant gene expression.

DETAILED DESCRIPTION OF THE PREFERRED EMBODIMENTS

The invention relates to the chemical synthesis of oligonucleotides and to chemical entities useful in such synthesis. The patents and publications identified in this specification are within the knowledge of those skilled in this field and are hereby incorporated by reference in their entirety.

The invention provides new processes for synthesizing oligonucleotides that allow for deprotection of the oligonucleotide under more rapid and more mild conditions than existing processes. The invention further provides a nucleoside base protecting group that is stable under oligonucleotide synthesis conditions, but which can be removed under more mild conditions than existing protecting groups, as well as nucleoside synthons having such base protecting groups. In addition, the invention provides oligonucleotides containing any of various base-sensitive functionalities, and methods for using such oligonucleotides to modulate specific gene expression.

In a first aspect, the invention provides a novel nucleoside base protecting group having the general structure I:

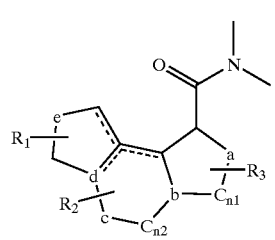

wherein n1, n2 and n3 are independently 0–10, wherein a, b, c, d and e are each independently hydrogen, carbon or nitrogen, and wherein the ring structure bearing substituent $R_3$ may be aromatic or heterocyclic, wherein the nitrogen displayed is the protected amino moiety of the nucleoside base, wherein $R_1$, $R_2$ and $R_3$ are independently hydrogen, or an alkyl, aryl, aralkyl, ether, hydroxy, nitrile, nitro, ester, carboxyl, or aldehyde group, and wherein dotted lines represent alternative exocyclic or endocyclic double bonds (i.e., any one of the dotted double bonds is present). In a preferred embodiment, a is hydrogen when n1 is 0 and is carbon or nitrogen when n1 is 1–10, b is hydrogen when n1, and n2 are both 0 and is carbon or nitrogen when either or both n1 and n2 are 1–10, c is hydrogen when n2 is 0 and is carbon or nitrogen when n2 is 1–10, and e is hydrogen when n3 is 0 and is carbon or nitrogen when n3 is 1–10. In a particularly preferred embodiment, compound I has n1, n2 and n3 values of 0, and a, b, c, d and e are each hydrogen, and the protecting group takes the form N-pent-4-enoyl, i.e., $CH_2=CH(CH_2)_2CO-$ (II). Compounds I and II protect the nucleoside base amino moieties by forming amide linkages, as in:

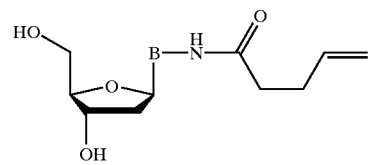

where the nitrogen displayed is the protected amino moiety of the nucleoside base B.

Base protecting group I and the preferred embodiment II are particularly advantageously used because such protecting group can be removed chemoselectively by treatment with a chemoselective removing agent. Thus, in a second aspect, the invention provides processes for synthesizing oligonucleotides which allow for removal of base protecting groups under more mild conditions than existing processes. In this process, nucleoside synthons having base protecting groups according to the invention are sequentially coupled according to standard procedures to yield a base-protected oligonucleotide. The base protecting groups are then removed by a chemoselective removing agent. For purposes of the invention, a nucleoside synthon means a monomeric or multimeric nucleoside derivative appropriate for synthesis of an oligonucleotide. Preferred nucleoside synthons include monomeric nucleoside phosphoramidites, phosphotriesters, or H-phosphonates having a blocked 5'-OH, preferably blocked with a trityl or dimethoxytrityl group. Alternatively, for 5' to 3' synthesis, the 3'-OH will be blocked and the leaving group will be at the 5' position. A chemoselective removing agent means an agent that is capable of removing a base protecting group according to the invention. In certain preferred embodiments, the chemoselective removing agent is selected from the group consisting of halogens, especially $Br_2$, $Cl_2$ and $I_2$, any of which are preferably taken up in water, or in pyridine/ROH, wherein R is an alkyl, aralkyl or aryl group having 1–10 carbon atoms, or as an N-halosuccinimide. In alternative embodiments, non-chemoselective reagents may be used, such as aqueous ammonium hydroxide, alcoholic ammonia, alkali carbonates in organic solvents, primary or secondary amines, alkali hydroxides, or any amidolytic reagent, i.e., an agent capable of hydrolyzing an amide linkage.

In one preferred embodiment, deprotection and cleavage of the oligonucleotide from the support can be rapidly carried out in a single step. In this embodiment, the support-bound, protected oligonucleotide is incubated in aqueous or alcoholic ammonia or alkyl amine. Preferably, such incubation will take place for about 15 minutes to about 10 hours, more preferably from about 1 hour to about 4 hours, and most preferably from about 1 hour to about 2 hours. The preferred temperature range for such incubation is from about 20° C. to about 70° C., more preferably from about 50° C. to about 60° C., and most preferably at about 55° C. When aqueous or alcoholic ammonia is used, the ammonia concentration is preferably from about 5% to saturated, which in the case of aqueous ammonia is about 28%. When alcoholic ammonia or alkyl amine is used, the alcohol is preferably a $C_1$–$C_{10}$ aliphatic alcohol, most preferably methanol or ethanol. When an alkyl amine is used, it is preferably a $C_1$–$C_{10}$ alkyl amine, most preferably methyl amine. This embodiment is particularly suitable for oligonucleotides having internucleoside linkages which are not labile in aqueous or alcoholic ammonia or alkyl amine, such as phosphodiester, phosphorothioate, phosphorodithioate, alkylphosphonate and non-phosphate linkages.

In another preferred embodiment, neutral conditions may be employed. In this embodiment, iodine/THF/$H_2O$ or N-iodosuccinimide/THF/$H_2O$ may be used. More preferably, the protected oligonucleotide is exposed to $I_2$ (most preferably about 0.45 M in pyridine) for a time sufficient to result in complete deprotection, most preferably for about 30 minutes or more.

In yet another preferred embodiment, anhydrous conditions may be employed to simultaneously deprotect the oligonucleotide and cleave it from the support. In this embodiment alcoholic $K_2CO_3$ is employed. Preferably the alcohol is a $C_1$–$C_{10}$ aliphatic alcohol, most preferably methanol. Incubation is preferably from about 20° C. to about 70°, more preferably from about 20° C. to about 30° C., and most preferably at about 25° C. The time for incubation is from about 15 minutes to about 6 hours, most preferably from about 3 hours to about 4 hours. The concentration of $K_2CO_3$ is preferably from about 0.005M to saturated, which in the case of $K_2CO_3$ in methanol is about 0.05 M. This embodiment is particularly attractive for synthesis of methylphosphotriester and phosphorothioate oligonucleotides.

In an additional preferred embodiment, simultaneous deprotection and cleavage from the support can be achieved through the use of $NH_3$ in DMF. Preferably, the ammonia in DMF will be saturated. The incubation will be from about 20° C. to about 70° C., more preferably from about 50° C. to about 70° C., and most preferably at about 65° C. This embodiment is particularly advantageous for synthesizing oligonucleotides containing primary phosphoramidate linkages, which are labile in $NH_4OH$.

In an additional preferred embodiment, simultaneous deprotection and cleavage from the support can be achieved through the use of $NH_3$ gas, preferably under pressure. More preferably, such deprotection is carried out at a pressure of from about 20 psi to about 200 psi, and most preferably from about 60 psi to about 120 psi. In one preferred embodiment, the deprotection reaction takes place in a glass pressure vessel, such as a Paar hydrogenation reactor, at a pressure of from about 20 psi to about 80 psi, most preferably at about 60 psi. In another preferred embodiment, the deprotection reaction can take place in a stainless steel reaction vessel, preferably at a pressure of from about 20 to about 200 psi, and most preferably from about 100 to about 120 psi. In either embodiment the reaction preferably takes place at from about 0° C. to about 100° C., and most preferably at about 25° C. Under these conditions the deprotection reaction preferably proceeds from about 1 hour to about 8 hours, most preferably from about 2 hours to about 4 hours. This embodiment also is particularly advantageous for synthesizing oligonucleotides containing primary phosphoramidate linkages, which are labile in $NH_4OH$.

The processes according to this aspect of the invention can utilize any suitable oligonucleotide synthesis chemistry in solid or solution phase, including the well known H-phophonate and phosphoramidite chemistries. In one preferred embodiment, synthesis is carried out on a suitable solid support using either H-phosphonate chemistry, phosphoramidite chemistry, or a combination of H-phosphonate chemistry and phosphoramidite chemistry (i.e., H-phosphonate chemistry for some cycles and phosphoramidite chemistry for other cycles). Suitable solid supports include any of the standard solid supports used for solid phase oligonucleotide synthesis, such as controlled-pore glass (CPG) or polymer supports. (See, e.g., Pon, Methods in Molec. Biol. 20: 465 (1993)). Synthesis on such a solid support begins with coupling a nucleoside synthon according to the invention to a nucleoside that is covalently linked the solid support (i.e., linked to a functionality on the solid support, preferably an amino or hydroxyl functionality). More generally, the processes according to this aspect of the invention can be used with any of the chemistries commonly used for oligonucleotide synthesis, whether in solution phase or in solid phase. Thus, in one preferred embodiment, the invention provides a process for synthesizing an oligonucleotide, such process comprising coupling a suitable nucleoside synthon, such as a nucleoside H-phosphonate, a nucleoside phosphoramidite, or a nucleoside phosphotriester to a nucleoside and deprotecting a nucleoside base with a reagent comprising (1) a halogen in water, in an ethereal solvent such as ether or THF, or in pyridine/ROH, wherein R is an alkyl, aralkyl or aryl group having 1–10 carbon atoms, or (2) a suitable halide releasing reagent, such as N-halosuccinimide sodium hypochlorite, or N-iodosuccinimide in paratoluenesulfonic acid. The nucleoside to which the nucleoside synthon is coupled may be a monomer, a multimer, or it may be the terminal nucleoside of a growing oligonucleotide chain. In either case, the nucleoside or growing oligonucleotide chain may be support-bound or free in solution.

The use of this new process provides numerous advantages. For example the process's mild procedure for removing the protecting group without affecting the integrity of other functionalities present in the oligonucleotide makes it possible to prepare novel analogs of oligonucleotides such as ribonucleoside-containing oligonucleotides, alkylphosphotriesters, certain base-sensitive phosphoramidate and other base-sensitive oligonucleotides. Surprisingly, the process according to the invention is more efficient than existing processes. This is believed to be due in part to the greater purity of the novel synthons according to the invention, relative to existing synthons.

One preferred use of this aspect of the invention is in the synthesis of oligonucleotides containing from one to about all ribonucleosides. Preferably, such synthesis employs a phosphoramidite, H-phosphonate or phosphotriester nucleoside monomer synthon having novel protecting groups according to the invention on the nucleoside base, as well as on the 2' hydroxyl of the nucleoside sugar.

Another preferred use of this aspect of the invention is in the synthesis of an oligonucleotide containing from one to about all primary phosphoramidate internucleoside linkages. The primary phosphoramidate internucleoside linkage has the structure:

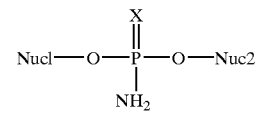

wherein "Nucl" represents the 3' position of a first nucleoside, "Nuc2" represents the 5' position of a second nucleoside, and X represents S or O. This process comprises condensing a nucleoside H-phosphonate with another nucleoside, wherein at least one of the nucleosides has a nucleoside base-protecting group according to the invention, to produce adjacent nucleosides coupled by an H-phosphonate internucleoside linkage, wherein at least one of the nucleosides has a nucleoside base-protecting group according to the invention, aminating the H-phosphonate internucleoside linkage to produce a primary phosphoramidate linkage, and chemoselectively removing the nucleoside base-protecting group without cleaving the primary phosphoramidate linkage. This process allows for synthesis, for the first time, of oligonucleotides containing primary phosphoramidate internucleoside linkages.

Another preferred use of this aspect of the invention is in the synthesis of oligonucleotides containing from one to about all alkylphosphonate internucleoside linkages, most preferably methylphosphonate internucleoside linkages. This new process comprises sequentially coupling nucleoside alkylphosphonamidite (preferably methylphosphonamidite) synthons having base protecting groups according to the invention to produce a base-protected oligonucleotide having an alkylphosphonate internucleoside linkage, followed by deprotection using a chemoselective removing agent. In one preferred embodiment, this aspect of the invention comprises coupling together an alkylphosphonamidite nucleoside synthon, most preferably a methylphosphonamidite nucleoside synthon, with a nucleoside or oligonucleoside having a free 5' hydroxyl group to produce a base-protected oligonucleotide having an alkylphosphonite (III) internucleoside linkage having as a bridging oxygen the oxygen from the free 5' hydroxyl group from the nucleoside or nucleotide, oxidizing the internucleoside linkage to an alkylphosphonate linkage, and deprotecting the oligonucleotide using a chemoselective removing agent. As used herein, the terms "nucleoside" or "oligonucleoside" include those having appropriately protected reactive functionalities, either in accordance with the present invention or with conventional protecting groups known in the art (see e.g Sonveaux in *Methods in Molecular Biology, Vol 26: Protocols for Oligonucleotide Conjugates* pp. 1–36 (S. Agrawal, Ed., Humana Press, 1994). Preferably, the oxidation of the internucleoside linkage to an alkylphosphonate linkage utilizes a phosphite oxidizing agent such as tert-butyl hydroperoxide or other well known agents (see Beaucage and Iyer, Tetrahedron 48: 2223–2311 (1992)).

Another preferred use of this aspect of the invention is in the synthesis of oligonucleotides containing from one to about all methylphosphotriester internucleoside linkages. The methylphosphotriester internucleoside linkage has the structure

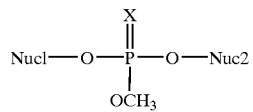

wherein "Nuc1" represents the 3' position of a first nucleoside, "Nuc2" represents the 5' position of a second nucleoside, and X is sulfur or oxygen.

One embodiment of this new process comprises condensing in the presence of 1H-tetrazole a methoxy-3'-O-(phosphoramidite)-5'-O-(4,4'-dimethoxytriphenyl)methyl nucleoside with another nucleoside, wherein at least one of the nucleosides has a nucleoside base-protecting group, to produce adjacent nucleosides coupled by a phosphite linkage, wherein at least one of the nucleosides has a nucleoside base-protecting group, oxidizing the internucleotidic phosphite linkage to yield an O-methylphosphotriester or O-methylphosphorothioate linkage, and chemoselectively removing the nucleoside base-protecting group without demethylating the O-methylphosphotriester or O-methylphophorothioate linkage(s). Another embodiment comprises condensing in the presence of a suitable activator, such as pivaloyl chloride, a nucleoside H-phosphonate or thio-H-phosphonate with another nucleoside, wherein at least at least one of the nucleosides has a nucleoside base protecting group, to produce adjacent nucleosides coupled by an H-phosphonate or thio-H-phosphonate linkage, wherein at least one of the nucleosides has a nucleoside base protecting group, oxidizing the H-phosphonate linkage in carbon tetrachloride/pyridine/methanol to produce an O-methylphosphotriester or O-methylphosphorothioate linkage, then chemoselectively removing the nucleoside base protecting group without memethylating the O-methylphosphotriester or O-methylphosphorothioate linkage, as described previously, and most preferably in $I_2$/pyridine/methanol.

The versatility of chemical synthetic approach of the processes according to this aspect of the invention makes such processes suitable for the synthesis of any of a broad class of compounds, all of which are referred to herein as "oligonucleotides". For purposes of the invention, the term oligonucleotide includes polymers of two or more deoxyribonucleotide, or any modified nucleoside, including 2'-halo-nucleosides, 2'O-substituted ribonucleosides, deazanucleosides or any combination thereof. Such monomers may be coupled to each other by any of the numerous known internucleoside linkages. In certain preferred embodiments, these internucleoside linkages may be phosphodiester, phosphotriester, phosphorothioate, or phosphoramidate linkages, or combinations thereof. The term oligonucleotide also encompasses such polymers having chemically modified bases or sugars and/or having additional substituents, including without limitation lipophilic groups, intercalating agents, diamines and adamantane. For purposes of the invention the term "2'-O-substituted" means substitution of the 2' position of the pentose moiety with a halogen (preferably Cl, Br, or F), or an —O-lower alkyl group containing 1–6 saturated or unsaturated carbon atoms, or with an —O-aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups; or such 2' substitution may be with a hydroxy group (to produce a ribonucleoside), an amino or a halo group, but not with a 2'-H group.

The use of this new process provides numerous advantages. For example the process's chemoselective capacity for removing the protecting group without affecting the integrity of other functionalities present in the oligonucleotide makes it possible to prepare novel analogs of oligonucleotides such as oligoribonucleotides, alkylphosphotriesters, certain base sensitive phosphoramidates and other base sensitive oligonucleotides. Besides being able to synthesize oligonucleotides bearing "sensitive" functionalities, it can also be used in the routine synthesis of various oligonucleotides as in case of the conventional protecting groups. In addition, this new process allows for synthesis of oligonucleotides still bound to any type of solid support. Where an unprotected, support bound oligonucleotide is desired, the full length support-bound oligonucleotide will have its internucleoside linkages oxidized, followed by contacting the oligonucleotide with a chemoselective removing agent to cleave the base protecting group. In the phosphoramidite approach, this is followed by treatment with anhydrous triethylamine to cleave the beta-cyanoethyl moiety.

Additionally, according to this aspect of the invention, support-bound branched oligonucleotides can be synthesized using, for example glycol residues in which one hydroxyl group is protected by e.g., DMT, and the other by a protecting group according to the invention. Then the DMT group may be selectively removed and an oligonucleotide synthesized from the resulting unprotected hydroxyl. Upon completion of that oligonucleotide, the hydroxyl moiety protected by the protecting group according to the invention can be deprotected with a chemoselective removing agent and another, different oligonucleotide synthesized from it.

In a third aspect, the invention provides novel synthons for use in synthesis of oligonucleotides having base-sensitive functionalities. One such novel synthon can be used to prepare portions of the oligonucleotide containing deoxyribonucleosides linked by any known internucleoside linkage. This monomer synthon according to the invention has the general structure III:

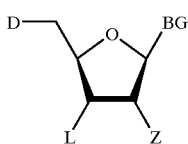

III wherein B is a nucleoside base, D is a 5'-OH blocking group (see e.g. Sonveaux in *Methods in Molecular Biology, Vol 26: Protocols for Oligonucleotide Conjugates* pp. 28–36 (S. Agrawal, Ed., Humana Press, 1994), preferably dimethoxytrityl or trityl, the protecting group (G) is the previously described structure I, or its preferred embodiment II, Z is hydrogen, —OG, —NG2, halogen (preferably Cl, Br or F), an —O-lower alkyl group containing 1–6 saturated or unsaturated carbon atoms, an —O-aryl or allyl group having 2–6 carbon atoms, wherein such alkyl, aryl or allyl group may be unsubstituted or may be substituted, e.g., with halogen, trifluoromethyl, cyano, nitroG, acylg, acyloxyG, alkoxyG, carboxyG, carbalkoxyG; and L is a phosphoramidite, H-phosphonate, or phosphotriester leaving group, including cyclic phosphoramidite leaving groups (see Iyer et al., J. Org. Chem. 60:5388–5389 (1995)). This synthon can be used alone, with any of the known synthons, or in conjunction with any of the following synthons. In an alternative embodiment, D can be a 3'-OH blocking group and L can be a 3' leaving group, for synthesis in the 5' to 3' direction. In another embodiment, the novel synthon can be a nucleoside dimer or multimer.

Another such novel synthon is useful in the synthesis of oligonucleotides containing ribonucleosides. This monomer synthon according to the invention has the general structure IV:

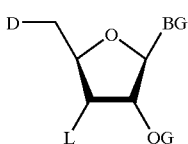

IV wherein B is a nucleoside base, D is a 5'-OH blocking group (see, e.g. Sonveaux in *Methods in Molecular Biology, Vol 26: Protocols for Oligonucleotide Conjugates* pp. 28–36 (S. Agrawal, Ed., Humana Press, 1994), preferably dimethoxytrityl or trityl, the protecting group (G) is the previously described structure I, or its preferred embodiment II, and L is a phosphoramidite, H-phosphonate, or phosphotriester leaving group, including cyclic phosphoramidite leaving groups (see Iyer et al., J. Org. Chem. 60:5388–5389 (1995)).

A scheme for synthesis of such a monomer having a particularly preferred embodiment of the protecting group according to the invention is shown in FIG. 1. According to this scheme, the monomer synthon is synthesized from the ribonucleoside by first protecting the 3' and 5' hydroxyl groups as the cyclic silyl ether derivative using the Markiewicz reagent. Then the N-pent-4-enoyl (PNT) group is installed at the nucleobase and the 2' hydroxyl of the ribose unit using PNT anhydride or using pent-4-enoic acid in the presence of dicyclohexylcarbodiimide (DCC). The 3' and 5' protecting groups are removed using tetrabutylammonium fluoride, followed by conversion of the diol to the 5'-O-4,4-dimethoxytrityl 3'-O-phosphoramidite monomer synthon by adaptation of standard phosphoramidite synthesis protocols using the appropriate chlorophosphitylation reagent. A minor isomerization product resulting from 2'-3' migration of groups is also formed, but is readily removed by chromatography. The formation of this minor product can also be substantially reduced by using bis-N,N-diisopropylphosphoramidite as the phosphitylating reagent.

Another novel synthon according to this aspect of the invention is useful for synthesizing oligonucleotides containing primary phosphoramidate internucleoside linkages. This monomer synthon according to the invention has the general structure V:

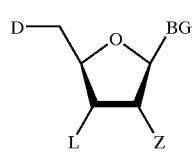

V wherein B is a nucleoside base, D is a 5'-OH blocking group (see e.g Sonveaux in *Methods in Molecular Biology, Vol 26: Protocols for Oligonucleotide Conjugates* pp. 28–36 (S. Agrawal, Ed., Humana Press, 1994), preferably dimethoxytrityl or trityl, the protecting group (G) is the previously described structure I, or its preferred embodiment II, Z is hydrogen, —OG, —NG2, halogen (preferably Cl, Br or F), an —O-lower alkyl group containing 1–6 saturated or unsaturated carbon atoms, an —O-aryl or allyl group having 2–6 carbon atoms, wherein such alkyl, aryl or allyl group may be unsubstituted or may be substituted, e.g., with halogen, trifluoromethyl, cyano, nitroG, acylg, acyloxyG, alkoxyG, carboxyG, carbalkoxyG; and L is an H-phosphonate or H-phosphonothioate (see Kers et al., Nucleosides and Nucleotides 15: 361–378 (1996)) leaving group.

Another novel synthon according to this aspect of the invention is useful for synthesizing oligonucleotides containing alkylphosphonate internucleoside linkages. This monomer synthon according to the invention has the general structure VI:

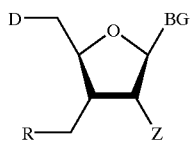

wherein B is a nucleoside base, D is a 5'-OH blocking group (see e.g. Sonveaux in *Methods in Molecular Biology, Vol 26: Protocols for Oligonucleotide Conjugates* pp. 28–36 (S. Agrawal, Ed., Humana Press, 1994), preferably dimethoxytrityl or trityl, R is an alkylphosphonamidite (preferably a methylphosphonamidite) group, Z is hydrogen, —OG, —NG2, halogen (preferably Cl, Br, or F), an —O-lower alkyl group containing 1–6 atoms, wherein such alkyl, aryl or allyl group may be unsubstituted or may be substituted, e.g., with halogen, trifluoromethyl, cyano, nitroG, acylG, acyloxyG, alkoxyG, carboxyG, carbalkoxyG; and the protecting group (G) is the previously described structure I, or its preferred embodiment II.

For purposes of this aspect of the invention, the term "alkyl group" means a lower alkyl group containing 1–6 saturated or unsaturated carbon atoms, or an allyl group having 2–6 carbon atoms, wherein such alkyl or allyl group may be unsubstituted or may be substituted, e.g., with halogen, hydroxy, trifluoromethyl, cyano, nitro, acyl, acyloxy, alkoxy, carboxyl, carbalkoxyl, or amino groups.

In a fourth aspect, the invention provides novel oligonucleotides containing from one to about all of a variety of base-sensitive functionalities. In a preferred embodiment, such oligonucleotides may contain from one to about all ribonucleotides and/or may contain from one to about all internucleoside linkages selected from the group consisting of primary phosphoramidate and methylphosphotriester linkages. In addition, oligonucleosides according to this aspect of the invention may have alkylphosphonate or alkylphosphonite (III) internucleoside linkages. In embodiments of oligonucleotides according to this aspect of the invention that have fewer than all primary phosphoramidate or methylphosphotriester internucleoside linkages, the other internucleoside linkages may be any of the known internucleoside linkages, or may be any internucleoside linkage not yet known that can be incorporated into an oligonucleotide according to a synthetic chemistry with which the process according to the invention is compatible. In certain preferred embodiments, the other internucleoside linkages are phosphodiester or phosphorothioate linkages. In the case of phosphorothioate internucleoside linkages, the linkages may be phosphorothioate mixed enantiomers or stereoregular phosphorothioates(see Iyer et al., Tetrahedron Asymmetry 6: 1051–1054 (1995).

Oligonucleotides containing such a mixture of internucleoside linkages are referred to herein as mixed backbone oligonucleotides. In some preferred embodiments of mixed backbone oligonucleotides according to the invention, the internucleoside linkages that are not primary phosphoramidate or methylphosphotriester linkages are selected from the group consisting of phosphodiester and phosphorothioate internucleoside linkages. In some preferred embodiments of mixed backbone oligonucleotides according to the invention, several adjacent nucleosides comprising one region of the oligonucleotide are connected by primary phosphoramidate or methylphosphotriester linkages, and several other adjacent nucleosides comprising another region of the oligonucleotide are connected by a different type of internucleoside linkage. These preferred oligonucleotides are referred to herein as "chimeric" oligonucleotides. In certain particularly preferred chimeric oligonucleotides according to the invention, the oligonucleotide comprises a primary phosphoramidate or methylphosphotriester region and a phosphorothioate and/or phosphodiester and/or alkylphosphonate region. In this context, a "primary phosphoramidate region" or a "methylphosphotriester region" is a region within an oligonucleotide of from about 2 to about 15 contiguous nucleosides linked to each other through primary phosphoramidate or methylphosphotriester linkages according to the invention, respectively. A "phosphorothioate region" is a region within an oligonucleotide of from about 4 to about 20 contiguous nucleosides linked to each other through phosphorothioate linkages. A "phosphodiester region" is a region within an oligonucleotide of from about 4 to about 20 contiguous nucleosides linked to each other through phosphodiester linkages. An "alkylphosphonate region" is a region within an oligonucleotide of from about 4 to about 20 contiguous nucleosides linked to each other through alkylphosphonate, preferably methylphosphonate linkages. In most preferred chimeric oligonucleotides according to the invention, the oligonucleotide comprises a phosphorothioate or phosphodiester region flanked on either side by a primary phosphoramidate or methylphosphotriester region, or alternatively, a primary phosphoramidate or methylphosphotriester region flanked on either side by a phosphorothioate or phosphodiester region. In one preferred embodiment the nucleosides of the primary phosphoramidate or methylphosphotriester region are ribonucleosides or 2'-O-substituted ribonucleotides, as defined above herein. Preferred chimeric oligonucleotides according to the invention are further characterized by having the ability to activate RNaseH.

Preferably, such oligonucleotides will have from about 12 to about 50 nucleotides, most preferably from about 17 to about 35 nucleotides. Preferably, such oligonucleotides will have a nucleotide sequence that is complementary to a genomic region, a gene, or an RNA transcript thereof. The term complementary means having the ability to hybridize to a genomic region, a gene, or an RNA transcript thereof under physiological conditions. Such hybridization is ordinarily the result of base-specific hydrogen bonding between complementary strands, preferably to form Watson-Crick or Hoogsteen base pairs, although other modes of hydrogen bonding, as well as base stacking can also lead to hybridization. As a practical matter, such hybridization can be inferred from the observation of specific gene expression inhibition. The gene sequence or RNA transcript sequence to which the modified oligonucleotide sequence is complementary will depend upon the biological effect that is sought to be modified. In some cases, the genomic region, gene, or RNA transcript thereof may be from a virus. Preferred viruses include, without limitation, human immunodeficiency virus (type 1 or 2), influenza virus, herpes simplex virus (type 1 or 2), Epstein-Barr virus, cytomegalovirus, respiratory syncytial virus, influenza virus, hepatitis B virus, hepatitis C virus and papilloma virus. In other cases, the genomic region, gene, or RNA transcript thereof may be from endogenous mammalian (including human) chromosomal DNA. Preferred examples of such genomic regions, genes or RNA transcripts thereof include, without limitation, sequences encoding vascular endothelial growth factor (VEGF), beta amyloid, DNA methyltransferase, protein kinase A, ApoE4 protein, p-glycoprotein, c-MYC protein, BCL-2 protein, protein kinase A and CAPL. In yet other cases, the genomic region, gene, or RNA transcript thereof may be from a eukaryotic or prokaryotic pathogen including, without limitation, *Plasmodium falciparum, Plasmodium malarie, Plasmodium ovale,* Schistosoma spp., and *Mycobacterium tuberculosis.*

In a fifth aspect, the invention provides methods for using oligonucleotides containing any of a variety of base-sensitive functionalities to control the expression of specific genes. Such methods comprise administering oligonucleotides according to the invention to cells or to animals, including humans. These methods may be used to assess gene function, or as a therapeutic approach to the treatment of diseases resulting from aberrant gene expression.

Due to the nonionic character of certain preferred base labile functionalities in oligonucleotides according to the invention, the invention further provides a method for therapeutically treating, with reduced side effects, a disease caused by aberrant gene expression, the method comprising administering to an individual having the disease a composition of matter comprising an oligonucleotide according to the invention, wherein the oligonucleotide is complementary to a gene that is aberrantly expressed, wherein such aberrant expression causes the disease. In this context, aberrant gene expression means expression in a host organism of a gene required for the propagation of a virus or a prokaryotic or eukaryotic pathogen, or inappropriate expression of a host cellular gene. Inappropriate host cellular gene expression includes expression of a mutant allele of a cellular gene, or underexpression or overexpression of a normal allele of a cellular gene, such that disease results from such inappropriate host cellular gene expression. Preferably, such administration should be parenteral, oral, sublingual, transdermal, topical, intranasal or intrarectal. Administration of the therapeutic compositions can be carried out using known procedures at dosages and for periods of time effective to reduce symptoms or surrogate markers of the disease. When administered systemically, the therapeutic composition is preferably administered at a sufficient dosage to attain a blood level of oligonucleotide from about 0.01 micromolar to about 10 micromolar. For localized administration, much lower concentrations than this may be effective, and much higher concentrations may be tolerated. Preferably, a total dosage of oligonucleotide will range from about 0.1 mg oligonucleotide per patient per day to about 200 mg oligonucleotide per kg body weight per day. It may be desirable to administer simultaneously, or sequentially a therapeutically effective amount of one or more of the therapeutic compositions of the invention to an individual as a single treatment episode. In a preferred embodiment, after the composition of matter is administered, one or more measurement is taken of biological effects selected from the group consisting of complement activation, mitogenesis and inhibition of thrombin clot formation.

The following examples further illustrate certain preferred embodiments of the invention and are not limiting in nature.

EXAMPLE 1

Preparation of N-pent-4-enoyl 2'-deoxy adenosine (dA Npr)

2'-Deoxyadenosine (Mallinckckrodt) (2.5 g, 10 mmol) was dried by repeated evaporation from anhydrous pyridine and was suspended in 50 ml of anhydrous pyridine. Trichloromethylsilane (64. ml, 50 mmol) was added and the reaction stirred for about 1 h. Then, 4-pentenoic anhydride (4 g, 20 mmol) was added and the contents stirred. After 15 min triethyl amine (3 ml) was added and the contents stirred for 2–3 h. The reaction slurry was cooled to 0–5° C. and 10 ml of water was added. After 5 min., 28% $NH_4OH$ (10 ml) was added. The resulting dear solution was evaporated to dryness. Water (150 ml) was added and the reaction mixture was extracted with ethylacetate: ether (50 ml, 1:1). The aqueous layer was separated and concentrated to a small volume. Upon leaving at room temperature, a white precipitate of the title compound was obtained. Alternatively, the title compound was purified by column chromatography followed by crystallization. Filtration and drying gave ca. 3.5 g of pure title compound. Several experiments repeating the above procedure, using larger scale of operation, gave the title compound in 85–90% yield.

The same general procedure can be employed for the preparation of dG and dC protected nucleosides.

EXAMPLE 2

Preparation of 5'-O-DMT-N-4-pent-4-enoyl-nucleoside synthons

The title compound was prepared by adopting a procedure as described by Froehler in Protocols for Oligonucleotides and analogs, Agrawal, S. Ed., pp. 63–80 as given below:

To 544 mg (1.63 mmol) of dA(N-pr) in 20 ml of anhydrous pyridine was added 1.108 g (3.3 mmol) of dimethoxytritylchloride. The reaction mixture was stirred at room temperature for 12 h. The reaction mixture was evaporated to dryness. The residue was chromatographed over silica gel 60 and eluted with $CH_2Cl_2:CH_3OH:(Et)_3N$ to give 0.73 of 5'-O-DMT-N-4-pent-4-enoyl-2'-deoxyadenosine as a white foamy material.

To a stirred solution of 1,2,4 triazole (0.944 g, 13.3 mmol) and triethylamine (5.5 ml, 30 mmol) in anhydrous $CH_2Cl_2$ (40 ml) was added $PCl_3$ (0.35 ml, 3.9 mmol) at room temperature under argon. After 30 min, the reaction mixture was cooled to 0° C. and 5'-DMT-protected nucleoside (500 mg, 0.88 mmol) in 15 ml $CH_2Cl_2$ was added dropwise over 10–15 min at 0° C. and allowed to warm to room temperature. The reaction mixture was poured into 1M triethylammonium bicarbonate (TEAB) (75 ml, pH 8.5) with stirring. The mixture was transferred to a separatory funnel and the phases separated. The aqueous phase was extracted with methylene chloride and the combined organic phase washed with 1M TEAB (1×50 ml). The organic layer was dried over sodium sulfate and evaporated to dryness. The solid product thus obtained was purified by chromatography over silica gel. Elution with $CH_2Cl_2:CH_3OH:(Et)_3N$ (18:1:1) gave 0.065 g of the title compound.

Other H-phosphonate nucleosides are similarly prepared in overall yields ranging from 70–90%.

Alternatively, phosphoramidite monomers were prepared according to standard procedures (see, e.g., Beaucage, Oligonucleotide Synthesis: Phosphoramidite Approach, In *Protocols for Oligonucleotides and Analogs,* S. Agrawal, Ed., Humana Press, Totowa, N.J., Vol. 20, pp. 33–61 (1993)).

EXAMPLE 3

Solid Phase Coupling of Nucleoside Synthons and Removal of Base Protecting Groups Nucleoside synthons prepared according to Example 2 were coupled using solid phase H-phosphonate methodology (Froehler ref. above). The support bound oligonucleotide H-phosphonate was then treated with a solution of 2% $I_2$ in (pyridine:water, 98:2) for 30 min. This procedure completely removes the base protecting groups. An additional step to oxidize the H-phosphonate internucleoside linkages is not necessary if one is making oligonucleotide phosphodiesters using H-phosphonate methodology because simultaneous oxidation and deprotection can be achieved in a single reaction using the $I_2$ reagent specified above. Otherwise, conversion of the internucleoside linkage to phosphorothioates, morpholidates, or alkyltriesters is carried out according to standard procedures. Rapid cleavage from the support can be achieved using aqueous $NH_4OH$ (28% at 55° C. for 1 hour).

EXAMPLE 4

Solid Phase Coupling of Nucleoside Synthons, Introduction of the Primary Phosphoramidate Linkage and Removal of Base Protecting Groups Nucleoside synthons prepared according to Example 2 were coupled using solid phase H-phosphonate methodology (Froehler ref. above). The support bound oligonucleotide H-phosphonate was then treated with a solution of $NH_3$ (0.5 M in dioxane/$CCl_4$, 1:1) at ambient temperature for 30 minutes to give the corresponding support-bound primary phosphoramidate dinucleotide. Exposure to a solution of 2% $I_2$ in pyridine:methanol (98:2) for 30 minutes, followed by treatment with a saturated solution of $NH_3$ in dioxane at 55° C. for 12–16 hours furnished the free primary phosphoramidate dinucleotide in greater than 97%. Alternatively, deprotection and cleavage from the support was carried out in ammonia gas under pressure. The reaction was carried out in 60 psi ammonia gas in a glass reaction vessel set up similar to the Paar hydrogenation reactor at room temperature for four hours, or in 100–120 psi ammonia gas in a stainless steel reaction vessel at room temperature for 24 hours. Deprotection and cleavage from the support was substantially complete in either case, without degradation of the primary phosphoramidate internucleoside linkage.

EXAMPLE 5

Relative Nuclease Resistance of Oligonucleotides Containing Primary Phosphoramidate Linkages Oligonucleotides containing either all primary phosphoramidate internucleoside linkages or a mixture of primary phosphoramidate internucleoside linkages and phosphorothioate or phosphodiester internucleoside linkages in various chimeric configurations are synthesized according to Example 4, or by incorporating the protocol of Example 4 into a conventional H-phosphonate or phosphoramidite synthetic approach. Oligonucleotide phosphodiesters and phosphorothioates are synthesized according to standard procedures. The oligonucleotides have a previously described sequence that is complementary to a portion of the gag gene of HIV-1 (see Agrawal and Tang, Antisense Research and Development 2: 2612–66(1992)).

To test the relative nuclease resistance of these oligonucleotides the oligonucleotides are treated with snake venom phosphodiesterase (SVPD). About 0.2 $A_{260}$ units of oligonucleotide is dissolved in 500 microliters buffer (40 mM $NH_4CO_3$, pH 7.0, 20 mM $MgCl_2$) and mixed with 0.1 units SVPD. The mixture is incubated at 37° C. for 420 minutes. After 0, 200 and 420 minutes, 165 microliter aliquots are removed and analyzed using ion exchange HPLC. Oligonucleotides containing primary phosphoramidate internucleoside linkages are expected to have greater nuclease resistance than oligonucleotides containing exclusively phosphodiester or phosphorothioate internucleoside linkages.

EXAMPLE 6

Duplex Stability of Oligonucleotides Containing Primary Phosphoramidate Internucleoside Linkages Oligonucleotides containing either all primary phosphoramidate internucleoside linkages or a mixture of primary phosphoramidate internucleoside linkages and phosphorothioate or phosphodiester internucleoside linkages in various chimeric configurations are synthesized according to Example 4, or by incorporating the protocol of Example 4 into a conventional H-phosphonate or phosphoramidite synthetic approach. Oligonucleotide phosphodiesters and phosphorothioates are synthesized according to standard procedures. The oligonucleotides have a previously described sequence that is complementary to a portion of the gag gene of HIV-1 (see Agrawal and Tang, Antisense Research and Development 2: 261–266(1992)). The oligonucleotides are tested for their ability to form duplexes with complementary oligodeoxyribonucleotides and oligoribonucleotides. In separate reactions, each oligonucleotide is mixed with an equivalent quantity (0.2 $A_{260}$ units) of its complementary oligonucleotide in 150 mM NaCl, 10 mM $Na_2PO_4$, 1 mM EDTA (pH 7.0). The mixture is heated to 85° C. for 5 minutes, then cooled to 30° C. The temperature is then increased from 30° C. to 80° C. at a rate of 1° C. per minute and $A_{260}$ is recorded as a function of temperature. Oligonucleotides according to the invention formed duplexes with complementary oligodeoxyribonucleotides or oligoribonucleotides at temperatures well above physiological temperatures.

EXAMPLE 7

Inhibition of HIV-1 by Oligonucleotides Containing Primary Phosphoramidate Internucleoside Linkages Oligonucleotides containing either all primary phosphoramidate internucleoside linkages or a mixture of primary phosphoramidate internucleoside linkages and phosphorothioate or phosphodiester internucleoside linkages in various chimeric configurations are synthesized according to Example 4, or by incorporating the protocol of Example 4 into a conventional H-phosphonate or phosphoramidite synthetic approach. Oligonucleotide phosphodiesters and phosphorothioates are synthesized according to standard procedures. The oligonucleotides have a previously described sequence that is complementary to a portion of the gag gene of HIV-1 (see Agrawal and Tang, Antisense Research and Development 2: 261–266(1992)).

Oligonucleotides are tested for their ability to inhibit HIV-1 in a tissue culture system. H9 lymphocytes are infected with HIV-1 virions (0.01–0.1 $TCID_{50}$/cell) for one hour at 37° C. After one hour, unadsorbed virions are washed away and the infected cells are divided among wells of 24 well plates. To the infected cells, an appropriate concentration (from stock solution) of oligonucleotide is added to obtain the required concentration (0.1–10 micromolar) in 2 ml media. The cells are then cultured for four days. At the end of four days, inhibition of HIV-1 is assessed by observing or measuring reductions in syncytium formation, p24 expression and reverse transcriptase activity. All of the tested oligonucleotides according to the invention are expected to show significant reductions in these parameters without significant cytotoxicity.

EXAMPLE 8

Preparation of 5'-O-DMT-N-4-pent-4-enoyl-nucleosides

To 544 mg (1.63 mmol) of dA(N-pr) in 20 ml of anhydrous pyridine was added 1.108 g (3.3 mmol) of dimethoxytritylchloride. The reaction mixture was stirred at room temperature for 12 h. The reaction mixture was evaporated to dryness. The residue was chromatographed over silica gel 60 and eluted with $CH_2Cl_2:CH_3OH:(Et)_3N$ to give 0.73 g of 5'-O-DMT-N-4-pent-4-enoyl-2'-deoxyadenosine as a white foamy material.

EXAMPLE 9

Synthesis of Nucleoside Methylphosphonamidite Monomer Synthons

Nucleoside methylphosphonamidite monomer synthons were synthesized as follows. In this experiment, the nucleoside bases were cytosine, adenine and guanine. Methyldichlorophosphine (3 mmol) was dissolved in anhydrous methylene chloride (5 ml) under argon. Anhydrous diisopropylamine (6 mmol) was added to the solution via syringe at room temperature. The reaction mixture was rapidly stirred and a solution of the appropriate protected nucleoside monomers (1 mmol in 5 ml anhydrous methylene chloride containing 1.5 mmol N,N-diisopropylethylamine), prepared according to Examples 1 and 8 above, was added. The reaction was allowed to continue for 20 minutes, then 0.5 ml anhydrous methanol was added to destroy any residual chlorophosphonite. The reaction mixture was poured into 5% aqueous sodium bicarbonate and the product was extracted with methylene chloride (3×20 ml). The combined extracts were dried over anhydrous $Na_2SO_4$ and evaporated to dryness. The residue for each of the protected nucleoside methylphosphonamidite monomer synthons thus obtained was purified by silica gel column chromatography. Elution gave the desired product amidites as white foams after drying in vacuo. Yields were 84% for C, 92% for A and 54% for G. Analysis by $^{31}P$-NMR ($CDCl_3$, trimethylphosphate as external standard) and FAB-MS ($M^+$ ion) gave the expected results for each amidite. The $R_P/S_P$ ratio was about 60/40. Each of the nucleoside monomer synthons was readily soluble in anhydrous acetonitrile.

EXAMPLE 10

Synthesis of Methylphosphonate Dinucleosides

Thymidine nucleoside coupled to a CPG support by its 3' hydroxyl functionality was prepared according to standard procedures. In separate reactions, each of the nucleoside monomer synthons prepared according to Example 9 were coupled to the support-bound thymidine using conventional phosphoramidite chemistry. The coupling reaction yielded a support bound dinucleoside coupled by an internucleosidic methylphosphonite (III) linkage. This linkage was then oxidized using tert-butyl hydroperoxide (1 M in toluene) to yield a methylphosphonate internucleosidic linkage. The support-bound methylphosphonate dinucleosides were then treated with aqueous ammonium hydroxide (28%, 1 hour, room temperature) to remove the PNT protecting group and to cleave the dimers from the solid support. The dimers were obtained in yields of 94–96% as a mixture of $R_P$, $S_P$ diastereomers. Analysis by HPLC confirmed that the dimers were identical to dimer standards prepared from commercially available phosphonamidite monomers using both tert-butyl hydroperoxide and iodine as oxidants and employing manufacturer-recommended deprotection conditions. Further analysis by $^{31}P$-NMR and MALDI-TOF mass spectroscopy also proved the authenticity of the dimers produced according to this example (data not shown).

EXAMPLE 11

Synthesis of Chimeric Oligonucleotides Containing Methylphosphonate Internucleosidic Linkages Nucleoside monomer synthons prepared according to Example 9 were used under standard phosphoramidite coupling conditions to prepare chimeric oligonucleotides having methylphosphonate internucleosidic linkages in different numbers and at different positions. All syntheses were carried out on a 1–10 micromole scale. A first oligonucleotide had its 5 most 5' internucleosidic linkages as methylphosphonates, with the remaining 9 internucleosidic linkages as phosphodiesters. A second oligonucleotide had its 10 most 5' internucleosidic linkages as methylphosphonates, with the remaining 9 internucleosidic linkages as phosphodiesters. A third oligonucleotide had 10 phosphodiester internucleosidic linkages, followed by 4 methylphosphonate internucleosidic linkages, followed by 4 phosphodiester internucleosidic linkages. A fourth oligonucleotide had 5 phosphodiester internucleosidic linkages, followed by 4 methylphosphonate internucleosidic linkages, followed by 9 phosphodiester internucleosidic linkages. Following synthesis, the support-bound oligonucleotides were treated with aqueous ammonium hydroxide (28% for 1 hour at room temperature) to remove the phosphate and nucleoside base protecting groups and cleave the oligonucleotides from the support. Polyacrylamide gel electrophoresis revealed that these oligonucleotides had identical mobility to oligonucleotide standards of the same structure prepared using commercially available monomer synthons under the conditions recommended by the manufacturer. Surprisingly, HPLC analysis demonstrated that the monomer synthons according to the invention gave a superior product/failure sequence ratio, relative to the commercially available monomer synthons.

EXAMPLE 12

Preparation of 5'-O-DMT-N-4-pent-4-enoyl-nucleoside amidites

The PNT nucleosides prepared according to Example 1 were employed in the synthesis of beta-cyanoethyl-(CEPNT) and methoxy-(MEPNT) 3'-O-(phosphoramidite)-5'-O-(4,4-dimethoxytriphenyl) methyl) [DMT] monomers according to standard procedures (see, e.g., Beaucage, Oligonucleotide Synthesis: Phosphoramidite Approach, In *Protocols for Oligonucleotides and Analogs*, S. Agrawal, Ed., Humana Press, Totowa, N.J., Vol. 20, pp. 33–61 (1993), except that oxidation of the phosphite linkage is accomplished by using tert-butyl hydroperoxide. Briefly, the PNT-nucleoside (1.5 g) was dissolved in dry pyridine (30 ml) and co-evaporated three times, then taken up in dry pyridine (20 ml). A solution of 4,4-dimethoxytrityl chloride (2.6 g) in dry pyridine (10 ml) was added over a period of 30 minutes. After stirring at ambient temperature for 1.5 hours, the solvent was evaporated. The residue was chromatographed on a silica gel column and eluted with $CH_2Cl_2/N(Et)_3/EtOH$ (100/3/3) to give 2.2 g (73%) of the DMT derivative. Purification was in the eluant $CH_2Cl_2/EtOac/N(Et)_3$ (19/1/1) for protected deoxyadenosine or $CH_2Cl_2/EtOAc/EtOH$ (100/100/1) for protected deoxyguanosine. To a solution of the product (2.24 g in 50 ml dry methylene chloride and 5 ml triethylamine) was added 2-cyanoethyl-N,N'-diisopropyl chlorophosphoramidite (0.94 g), followed by stirring at room temperature for 3 hours. The reaction mixture was quenched by adding ice cold $NaHCO_3$ solution (5%, 40 ml). The solution was extracted with $CH_2Cl_2$ and the methylene chloride layer was dried over $Na_2SO_4$. The solvent was removed in vacuo and the residue was chromatographed on a silica gel column and eluted with $CH_2Cl_2/EtOAc/N(Et)_3$ (6/4/0.5) to yield 2.5 g CEPNT amidite as a white foam. For MEPNT amidites, N,N'-diisopropyl methylphosphonamidic chloride was substituted in place of 2-cyanoethyl N,N'- diiisopropyl chlorophosphoramidite in the protocol described above. The nucleoside phosphoramidites were fully characterized and the following spectral data was obtained.

MEPNT (dA). White foam; overall yield of 70–72%

$^{31}$P-NMR (CDCl$_3$): δ147.04, 146.90 ppm (ca. R$_P$:S$_P$, 1:1 mixture)

$^1$H-NMR (CDCl$_3$): δ8.61 (1H, s), 8.55 (1H, br), 8.17 (1H, s), 7.42–7.19 (9H, m), 6.82–6.75 (4H, m), 6.48 (1H, dd, J=2.9, 6.4 Hz), 5.93 (1H, ddt, J=6.5, 10.3, 17 Hz) 5.13 (1H, dd, J=17.0, 1.4 Hz), 5.04 (1H, dd, J=1.4, 10.3 Hz), 4.82–4.70 (1H, m), 4.38–4.28 (1H, m), 3.8 (6H, s), 3.58 (2H, m), 3.49 (2H, m, $^3J_{P-H}$=18.1 Hz, J=6.8 Hz), 3.35 (3H, d, $^3J_{P-H}$=13.4 Hz), 3.0 (2H, t, J=7.4 Hz), 2.87 (1H, m), 2.66 (1H, m), 2.53 (2H, m), 1.17 (12H, dd, J=6.8 Hz, $^4J_{P-H}$=2.4 Hz)

FAB-MS: Calcd for C$_{43}$H$_{53}$N$_6$O$_7$P, 797 (M+H)$^+$; Found m/z 797.

MEPNT (dC). Pale yellow foam; overall yield of 74–76%

$^{31}$P-NMR (CDCl$_3$): δ147.49, 146.81 ppm (ca. R$_P$:S$_P$, 1:1 mixture).

$^1$H-NMR (CDCl$_3$): δ10.0 (1H, br), 8.24 (1H, d, J=7.4 Hz), 8.18 (1H, d, J=7.4 Hz), 7.40–7.08 (9H, m), 6.84–6.76 (4H, m), 6.17 (1H, dd, J=6.3, 5.1 Hz), 5.78 (1H, ddt, J=6.4, 10, 16.9 Hz), 5.02 (1H, dd, J=1.4,17,3 HZ), 4.94 (1H, dd, J=1.4, 10.2 Hz), 4.62–4.54 (1H, m), 4.08 (1H, m), 3.61 (6H, s), 3.56–3.40 (4H, m), 3.26 (3H, d, $^3J_{P-H}$=13.2 Hz), 2.88–2.57 (3H, m), 2.40–2.34 (2H, m), 2.24–2.18 (1H, m), 1.02 (12H, d, J=6.7 Hz).

FAB-MS: Calcd. for C$_{42}$H$_{53}$N$_4$O$_8$P, 773 (M+H)$^+$; Found m/z, 773.

MEPNT (dG) White foam; overall yield of 70–72%

$^{31}$P-NMR (CDCl$_3$): δ146.78, 146.74 ppm (ca. R$_P$:S$_P$, 1:1 mixture)

$^1$H-NMR (CDCl$_3$): δ8.02 (1H, br), 7.92 (1H, s), 7.80 (1H, s), 7.43–7.20 (9H, m), 6.80–6.69 (4H, m), 6.20 (1H, dd, J=5.6, 7.9 Hz), 5.68 (1H, m), 4.96 (1H, dd, J=1.5, 17.1 Hz), 4.94 (1H, dd, J=1.5, 9.3 Hz), 4.72–4.63 (1H, m), 4.14–4.07 (1H, m), 3.63 (6H, s), 3.57–3.36 (4H, m), 3.29 (3H, d, $^3J_{P-H}$=13.2 Hz), 3.08 (2H, m), 2.84–2.76 (1H, m), 2.59–2.46 (1H, m), 2.24 (2H, m), 1.02 (12H, d, J=6.7 Hz)

FAB-MS: Calcd for C$_{43}$H$_{53}$N$_6$O$_8$P, 813 (M+H)$^+$; Found m/z, 813

CEPNT (dA). White foam; overall yield of 70–71%

$^{31}$P-NMR (CDCl$_3$); δ146.9, 146.81 ppm (ca. R$_P$:S$_P$, 1:1 mixture)

$^1$H-NMR (CDCl$_3$): δ8.60 (1H, br), 8.58 (1H, s), 8.15 (1H, s), 7.40–7.25 (9H, m), 6.81–6.70 (4H, m), 6.43 (1H, dd, J=2.4, 6.6 Hz), 5.90 (1H, ddt, J=6.5, 10.3, 16.9 Hz), 5.1 (1H, dd, J=1.5,17.1 Hz), 5.02 (1H, dd, 1.5, J=10 Hz), 4.78 (1H, m), 4.30 (1H, m), 4.20–4.07 (2H, m, 3.74 (6H, s), 3.63–3.54 (2H, m), 3.48 (2H, m), 3.40–3.31 (2H, m), 2.98 (2H, t, J=7.3 Hz), 2.6 (1H, m), 2.53–2.41 (3H, m), 1.16 (12H, d, J=6.6 Hz).

FAB-MS: Calcd for C$_{45}$H$_{54}$N$_7$O$_7$P, 836.3900 (M+H)$^+$; Found, m/z, 836.3899.

CEPNT (dC). Yellow foam; overall yield 72–75%

31P-NMR (CDCl$_3$); δ147.42, 146.81 ppm (ca. R$_P$:S$_P$, 1:1 mixture)

$^1$H-NMR (CDCl$_3$): δ9.75 (1H,br), 8.20 (1H, d, J=7.3 Hz), 7.43–7.20 (9H, m), 7.24 (1H, d, J=7.3 Hz), 6.75–6.56 (4H, m), 6.22 (1H, t, J=6.1 Hz), 5.8 (1H, ddt, J=6.3, 10.2, 16.6 Hz), 5.05 (1H, dd, J=1.4, 17.1 Hz), 4.98 (1H, dd, J=1.4, 10.3 Hz), 4.60 (1H, m), 4.23–4.12 (3H, m), 3.76 (6H, s), 3.66–3.33 (6H, m), 2.58 (2H, t, J=6.6 Hz), 2.41 (3H, m), 2.3 (1H, m), 1.1 (12H, d, J=6.3 Hz).

FAB-MS; Calcd for C$_{44}$H$_{54}$N$_5$O$_8$P, 812.3788 (M+J)$^+$; Found m/z, 812.3798.

CEPNT (dG). White foam; overall yield of 70–72%

$^{31}$P-NMR (CDCl$_3$): δ146.89, 146.83 ppm (ca. R$_P$:S$_P$, 1:1 mixture).

$^1$H-NMR (CDCl$_3$): δ8.04 (1H, br), 7.95 (1H, s), 7.82 (1H, s), 7.43–7.25 (9H, m), 6.82–6.69 (4H, m), 6.25 (1H, dd, J=5.6, 7.8 Hz), 5.70 (1H, m), 5.00 (1H, dd, J=1.5, 17 Hz), 4.95 (1H, dd, J=1.5, 9.5 Hz), 4.70–4.60 (1H, m), 4.15–4.06 (3H, m), 3.65 (6H, s), 3.58–3.20 (6H, m), 2.60 (2H, t, J=6.6 Hz), 2.45 (1H, m), 2.28 (3H, m), 1.09 (12H, d, J=6.4 Hz).

FAB-MS: Calcd for C$_{45}$H$_{54}$N$_7$O$_8$P, 852.3850 (M+H)$^+$, Found m/z, 852.3869.

EXAMPLE 13

Solid Phase Coupling of Nucleoside Amidites, Introduction of the Methyl Phosphotriester Linkage and Removal of Base Protecting Groups Methoxy-(MEPNT) 3'-O-(phosphoramidite)-5'-O-(4,4-dimethoxytriphenyl) methyl) [DMT] monomers were coupled in a standard 1H-tetrazole-mediated phosphoramidite coupling reaction to form the dinucleoside phosphites. The dinucleoside phosphites were then oxidized using t-butyl hydroperoxide (1M in toluene) to yield the protected O-methyl phosphotriester, or 3H-benzodithiol-3-one 1,1-dioxide to yield the protected O-methyl phosphorothioate. Subsequent exposure to iodine reagent (2% I$_2$ in pyridine/MeOH, 98/2) at room temperature for 30 minutes completely removed the base protecting groups to give CPG-bound dinucleoside methyl phosphotriesters. Cleavage from the support using anhydrous K$_2$CO$_3$ (0.05 M in MeOH) at room temperature for eight hours gave free dinucleoside methyl phosphotriesters in 95–97% yield as R$_P$ and S$_P$ diastereomeic mixtures. The products were analyzed by HPLC (see Iyer et al, Bioorg. Chem. 6: 1 (1995)).

EXAMPLE 14

Synthesis of Triester-Containing Chimeric Oligonucleotides

The CEPNT and MEPNT monomers were used to prepare chimeric trinucleotides having one phosphodiester or phosphorothioate internucleoside linkage and one O-methyl phosphotriester or phosphorothioate internucleoside linkage under conditions as described in Example 13. Synthesis was carried out on a solid support using conventional succinyl-linked nucleoside loading. The phosphodiester or phosphorothioate internucleoside linkage was assembled using the CEPNT monomer and the O-methyl phosphotriester or phosphorothioate internucleoside linkage was assembled using the MEPNT monomer. The trimers thus obtained, a mixture of four diastereomers, were characterized by $^{31}$P-NMR and $^1$H-NMR and by MALDI-TOF mass spectroscopy. In the $^{31}$P-coupled $^1$H-NMR, the OCH$_3$ protons appeared as four sets of doublets, indicating the presence of the four diastereomers (data not shown). The MALDI-TOF mass spectrum revealed the expected molecular ion at 911.7 (Na$^+$ form) for the species containing the phosphorothioate and O-methylphosphorothioate linkages.

This strategy was extended to the synthesis of support-bound nonanucleotide chimeras incorporating four phosphorothioate internucleotide linkages and either four S- or O-methylphosphotriester internucleotide linkages. In each case, $^{31}$P-NMR analysis proved that the methylphosphotriester and phosphorothioate segments were present in the correct relative proportion (data not shown). In addition, these chimeras exhibited slower mobility on polyacrylamide gel electrophoresis than a phosphodiester-phosphororthioate chimera of identical sequence (data not shown). These results demonstrate that the mild deprotection conditions according to the invention allow the synthesis of any chimeric oligonucleotide containing these base-sensitive internucleotide linkages.

EXAMPLE 15

Relative Nuclease Resistance of Oligonucleotides Containing Methyl Phosphotriester Linkages Oligonucleotides containing either all methyl phosphotriester internucleoside linkages or a mixture of methyl phosphotriester internucleoside linkages and phosphorothioate or phosphodiester internucleoside linkages in various chimeric configurations were synthesized according to Example 13 or 14. Oligonucleotide phosphodiesters and phosphorothioates were synthesized according to standard procedures.

To test the relative nuclease resistance of these oligonucleotides the oligonucleotides were treated with snake venom phosphodiesterase (SVPD). About 0.2 $A_{260}$ units of oligonucleotide was dissolved in 500 microliters buffer (40 mM $NH_4CO_3$, pH 7.0, 20 mM $MgCl_2$) and mixed with 0.1 units SVPD. The mixture was incubated at 37° C. for 420 minutes. After 0, 200 and 420 minutes, 165 microliter aliquots were removed and analyzed using ion exchange HPLC. Oligonucleotides containing methyl phosphotriester internucleoside linkages exhibited greater nuclease resistance than oligonucleotides containing exclusively phosphodiester or phosphorothioate internucleoside linkages.

EXAMPLE 16

Duplex Stability of Oligonucleotides Containing Methyl Phosphotriester Internucleoside Linkages Oligonucleotides containing either all methyl phosphotriester internucleoside linkages or a mixture of methyl phosphotriester internucleoside linkages and phosphorothioate or phosphodiester internucleoside linkages in various chimeric configurations were synthesized using the process described in Example 13 or 14. Oligonucleotide phosphodiesters and phosphorothioates were synthesized according to standard procedures. The oligonucleotides are tested for their ability to form duplexes with complementary oligodeoxyribonucleotides and oligoribonucleotides. In separate reactions, each oligonucleotide was mixed with an equivalent quantity (0.2 $A_{260}$ units) of its complementary oligonucleotide in 150 mM NaCl, 10 mM $Na_2PO_4$, 1 mM EDTA (pH 7.0). The mixture was heated to 85° C. for 5 minutes, then cooled to 30° C. The temperature was then increased from 30° C. to 80° C. at a rate of 1° C. per minute and $A_{260}$ was recorded as a function of temperature. Oligonucleotides according to the invention were found to form duplexes with complementary oligodeoxyribonucleotides or oligoribonucleotides at temperatures well above physiological temperatures.

EXAMPLE 17

Inhibition of HIV-1 by Oligonucleotides Containing Methyl Phosphotriester Internucleoside Linkages Oligonucleotides containing either all methyl phosphotriester internucleoside linkages or a mixture of methyl phosphotriester internucleoside linkages and phosphorothioate or phosphodiester internucleoside linkages in various chimeric configurations are synthesized according to the process described in Examples 13 or 14. Oligonucleotide phosphodiesters and phosphorothioates are synthesized according to standard procedures. The oligonucleotides have a previously described sequence that is complementary to a portion of the gag gene of HIV-1 (see Agrawal and Tang, Antisense Research and Development 2: 261–266(1992)).

Oligonucleotides are tested for their ability to inhibit HIV-1 in a tissue culture system. H9 lymphocytes are infected with HIV-1 virions (0.01–0.1 $TCID_{50}$/cell) for one hour at 37° C. After one hour, unadsorbed virions are washed away and the infected cells are divided among wells of 24 well plates. To the infected cells, an appropriate concentration (from stock solution) of oligonucleotide is added to obtain the required concentration (0.1–10 micromolar) in 2 ml media. The cells are then cultured for four days. At the end of four days, inhibition of HIV-1 is assessed by observing or measuring reductions in syncytium formation, p24 expression and reverse transcriptase activity. All of the tested oligonucleotides according to the invention are expected to show significant reductions in these parameters without significant cytotoxicity.

EXAMPLE 18

Rapid Oligonucleotide Synthesis Using CEPNT Amidites

Amidites were prepared as described in Example 12 above. Coupling was carried out using standard amidite chemistry. Following synthesis, the CPG-bound oligonucleotide was treated with aqueous $NH_4OH$ (28% in 10 ml $H_2O$) at 55° C. for 2 hours and the solution was evaporated on a speed vac to obtain the crude product. Alternatively, deprotection and cleavage from the support was carried out in ammonia gas under pressure. The reaction was carried out in 60 psi ammonia gas in a glass reaction vessel set up similar to the Paar hydrogenation reactor at room temperature for four hours, or in 100–120 psi ammonia gas in a stainless steel reaction vessel at room temperature for 2–4 hours. Analysis by CE and ion-exchange chromatography confirmed that the product was fully deprotected.

What is claimed is:

1. A process for synthesizing an oligonucleotide, the process comprising coupling to a nucleoside a nucleoside synthon having a nucleoside base protecting group having the structure

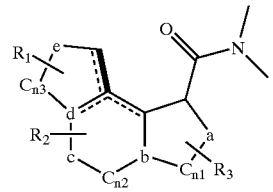

wherein n1, n2 and n3 are independently 0–10, wherein a, b, c, d and e are each independently hydrogen, carbon or nitrogen, and wherein the ring structure bearing substituent $R_3$ is aromatic or heterocyclic, wherein the nitrogen displayed is the protected amino moiety of the nucleoside base, wherein $R_1$, $R_2$ and $R_3$ are independently hydrogen, or an alkyl, aryl, aralkyl, ether, hydroxy, nitrile, nitro, ester, carboxyl, or aldehyde group, and wherein dotted lines represent alternative exocyclic or endocyclic double bonds; and removing the nucleoside base protecting group in ammonia gas.

2. The process according to claim 1, wherein a is hydrogen when n1 is 0 and is carbon or nitrogen when n1 is 1–10, b is hydrogen when n1 and n2 are both 0 and is carbon or nitrogen when either or both n1 and n2 are 1–10, c is hydrogen when n2 is 0 and is carbon or nitrogen when n2 is 1–10, and e is hydrogen when n3 is 0 and is carbon or nitrogen when n3 is 1–10.

3. The process according to claim 2, wherein n1, n2 and n3 are each 0 and a, b, c, d and e are each hydrogen.

4. The process according to claim 1, wherein the protecting group is N-pent-4-enoyl.

5. The process according to claim 1, wherein the nucleoside is covalently bound to a suitable solid support.

* * * * *